(12) United States Patent
   Simonot

(10) Patent No.: US 10,209,222 B2
(45) Date of Patent: Feb. 19, 2019

(54) METHOD FOR EDDY CURRENT TESTING

(71) Applicant: Airbus Operations SAS, Toulouse (FR)

(72) Inventor: Nicolas Simonot, Toulouse (FR)

(73) Assignee: Airbus Operations SAS, Toulouse (FR)

( * ) Notice: Subject to any disclaimer, the term of this patent is extended or adjusted under 35 U.S.C. 154(b) by 28 days.

(21) Appl. No.: 15/192,506

(22) Filed: Jun. 24, 2016

(65) Prior Publication Data

US 2016/0377576 A1    Dec. 29, 2016

(30) Foreign Application Priority Data

Jun. 25, 2015 (FR) ...................................... 15 55844

(51) Int. Cl.
  *G01N 27/90*  (2006.01)
(52) U.S. Cl.
  CPC .................................. *G01N 27/902* (2013.01)
(58) Field of Classification Search
  None
  See application file for complete search history.

(56) References Cited

U.S. PATENT DOCUMENTS

| 2,574,840 | A |   | 11/1951 | Jean et al. |
| 5,397,304 | A |   | 3/1995 | Truckai |
| 6,207,030 | B1 | * | 3/2001 | Zdunek ................ G01B 5/066 204/286.1 |
| 8,723,513 | B2 | * | 5/2014 | Ahn .................... G01N 27/9006 324/238 |
| 2004/0075432 | A1 |  | 4/2004 | Loud |
| 2006/0076669 | A1 |  | 4/2006 | Yu |
| 2011/0018530 | A1 |  | 1/2011 | Bousquet et al. |
| 2011/0260721 | A1 | * | 10/2011 | Fischer .................. G01B 7/105 324/229 |
| 2014/0330074 | A1 | * | 11/2014 | Morriss .............. A61B 17/1657 600/104 |
| 2014/0360289 | A1 | * | 12/2014 | Georgeson ............. G01D 11/30 73/866.5 |

OTHER PUBLICATIONS

French Search Report, dated Apr. 12, 2016, priority document.

* cited by examiner

*Primary Examiner* — Melissa J Koval
*Assistant Examiner* — Nasima Monsur
(74) *Attorney, Agent, or Firm* — Greer, Burns & Crain, Ltd.

(57) ABSTRACT

A method for testing the integrity of a component in a measurement area of the component, using an instrument having a flexible part and a rigid end part following the flexible part and carrying an eddy current probe. The method comprises a selection step in which a template corresponding to the measurement area is selected, a shaping step in which the flexible part is shaped against the template thus selected, a positioning step, in which the instrument thus shaped is positioned so that the eddy current probe is placed in the measurement area, and a measurement step, in which a measurement is made via the eddy current probe which has been thus positioned.

9 Claims, 2 Drawing Sheets

METHOD FOR EDDY CURRENT TESTING

CROSS-REFERENCES TO RELATED APPLICATIONS

This application claims the benefit of the French patent application No. 1555844 filed on Jun. 25, 2015, the entire disclosures of which are incorporated herein by way of reference.

BACKGROUND OF THE INVENTION

The present invention relates to a method for testing the integrity of a component using an instrument including an eddy current probe, and a toolkit comprising this instrument.

The testing of the integrity of a component, particularly an aircraft component, by means of an eddy current probe is a commonly used procedure, since it enables non-invasive testing to be performed.

More particularly, in the case of the testing of thrust reversers of aircraft engines, the protective casings have to be removed for access to the thrust reverser structure to be tested.

This procedure is therefore relatively lengthy and costly in terms of time and labor.

SUMMARY OF THE INVENTION

One object of the present invention is to provide a test method which enables the integrity of a structure to be tested simply and rapidly without the need to remove the surrounding parts.

For this purpose, a method is proposed for testing the integrity of a component in a measurement area of the component, using an instrument having a flexible part and a rigid end part following the flexible part and carrying an eddy current probe, the method comprising:

a selection step in which a template corresponding to the measurement area is selected, a shaping step in which the flexible part is shaped against the template thus selected, a positioning step, in which the instrument thus shaped is positioned so that the eddy current probe is placed in the measurement area, and a measurement step, in which a measurement is made by means of the eddy current probe which has been thus positioned.

Thus this verification method can be used to reach the various measurement areas of the component to be tested, resulting in an appreciable time saving.

Advantageously, the test method comprises, before the selection step, a production step in which the template corresponding to the measurement area is fabricated.

Advantageously, the movement from one measurement area to another consists in rotating the straight rigid end part through 180° about its longitudinal axis.

The invention also proposes a toolkit including a flexible part, a rigid end part following the flexible part and carrying an eddy current probe, and a set of templates arranged to shape the flexible part.

BRIEF DESCRIPTION OF THE DRAWINGS

The aforementioned characteristics of the invention, as well as others, will be more fully apparent from a perusal of the following description of an exemplary embodiment, the description being provided in relation to the attached drawings, of which.

DETAILED DESCRIPTION OF THE PREFERRED EMBODIMENTS

Figure 1:
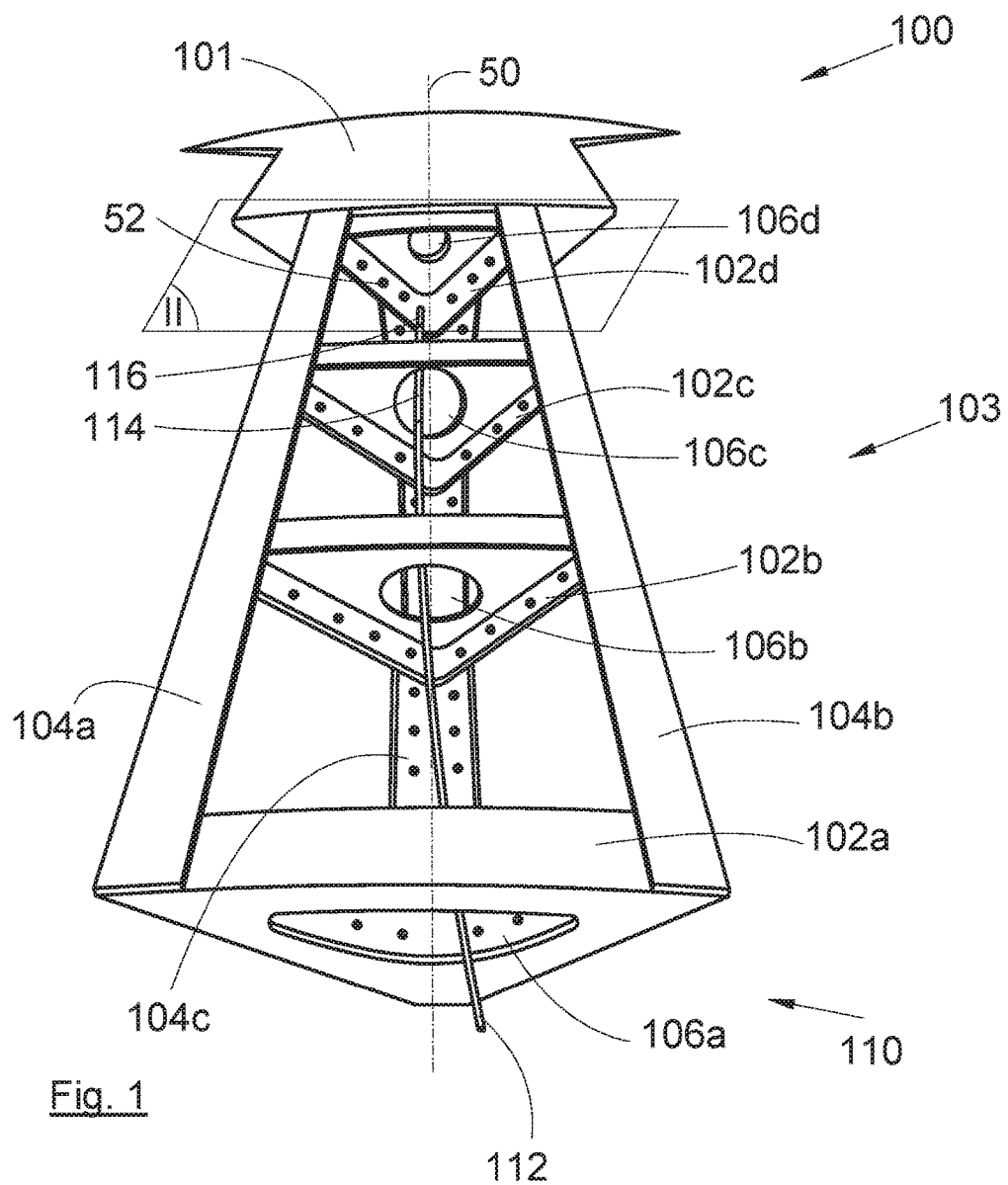
FIG. 1 is a perspective view of a structure of a thrust reverser of an aircraft engine, on which the test method as claimed in the invention is used.

FIG. 1 shows a thrust reverser 100 of an aircraft engine. The reverser 100 has a flap 101 and a structure 103, to one end of which the flap 101 is fixed. The structure 103 has a shape which is elongated parallel to a longitudinal axis 50. The structure 103 takes the form of a plurality of frames 102a-d assembled on three longitudinal members 104a-c parallel to the longitudinal axis 50. The fixing is carried out by welding and/or by installing screw and nut systems 52.

Each frame 102a-d has an opening 106a-d which allows the passage of electrical cables, among other things, along the structure 103.

The openings 106a-d also enable an instrument 110 having an eddy current probe (as it is known in the English terminology) to be inserted in order to reach the frame 102d nearest to the flap 101, for testing the integrity of the frame.

Figure 2:
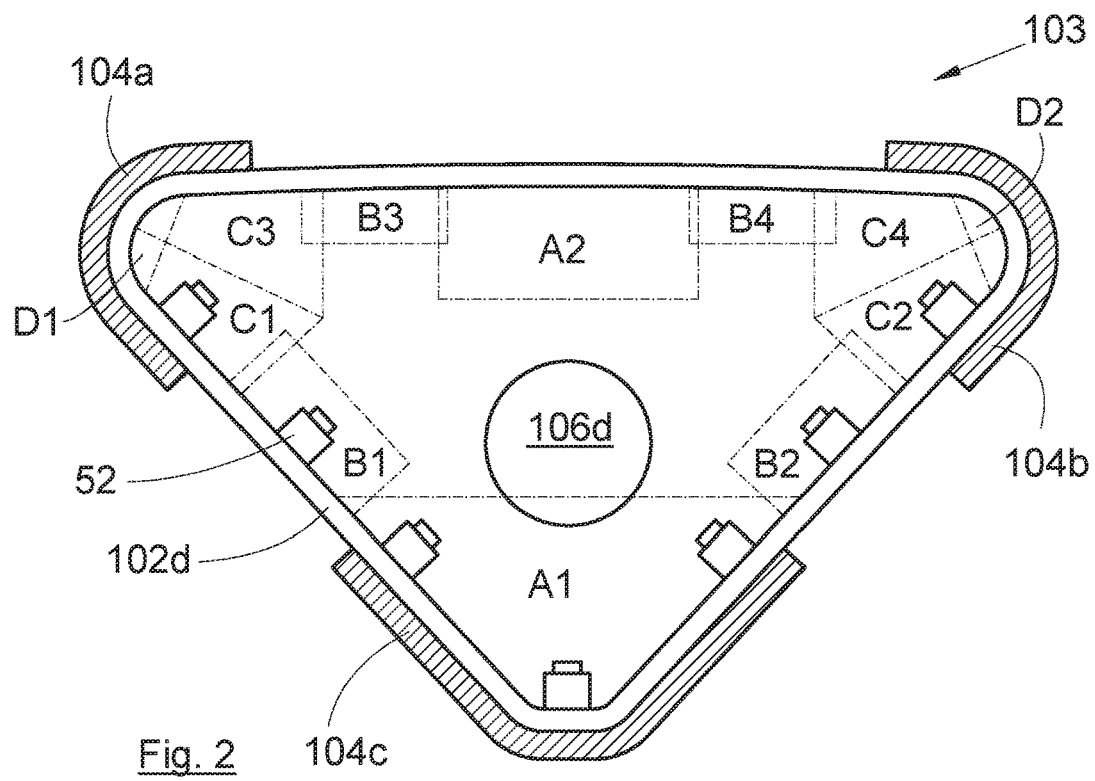
FIG. 2 is a sectional view of the structure of the thrust reverser along the plane II of FIG. 1.

FIG. 2 shows the structure 103 in cross section, facing the frame 102d nearest to the flap 101, in a view taken through the plane II, which is perpendicular to the longitudinal axis 50.

The frame 102d delimits an interior space which is virtually divided into a plurality of measurement areas, delimited in this case by thin chained lines. The measurement areas are given the references A1-2, B1-4, C1-4 and D1-2, and are the areas in which the eddy current probe is applied to make the measurements and thus test the integrity of the frame 102d.

Because of the symmetry of the frame 102d, the measurement areas are also symmetrical. To ensure that the whole of the frame 102d is covered, the measurement areas overlap one by one.

The testing of the integrity of the frame 102d comprises placing the eddy current probe 110 along all the surfaces of the frame 102d, moving from one measurement area to another. The measurement provided by the eddy current probe in a measurement area can then be used to test the integrity of the frame 102d in this measurement area.

Figure 3:
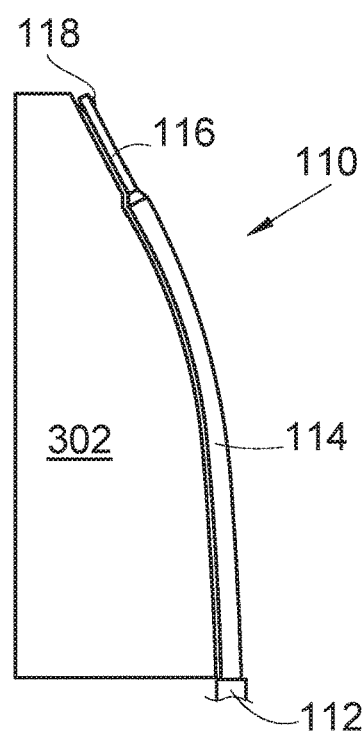
FIG. 3 shows a first example of the shaping of an eddy current probe instrument as claimed in the invention.
Figure 4:
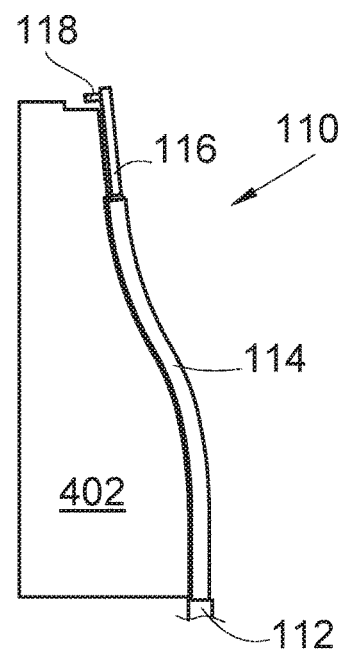
FIG. 4 shows a second example of the shaping of the instrument.

FIG. 3 shows the shaping of the instrument 110 to reach the areas referenced B1 and B4, and FIG. 4 shows the shaping of the instrument 110 to reach the areas referenced D1 and D2.

The instrument 110 has a rigid straight part 112 by which it can be held by a technician, a flexible part 114 following the straight part 112, and a rigid end part 116 following the flexible part 114 and carrying the eddy current probe 118.

A template 302, 402 is provided for each measurement area. The template 302, 402 has the shape that must be imparted to the flexible part 114 to enable the eddy current probe 118 to be positioned against the surface of the frame 102d in the measurement area associated with the template 302, 402. Thus, the flexible part 114 has a single curve in the case of FIG. 3, and the flexible part 114 has a double curve in the case of FIG. 4. The template 302, 402 is made of a material which is rigid enough not to be deformed under the pressure of the flexible part 114. Each template depends on the various measurement areas of the structure 103 to be tested, and the positioning of templates 302 and 402 enables the repeatability of the measurements to be improved. A template 302, 402 corresponds to a measurement area when it enables the flexible part 114 to be orientated in accordance with the measurement area to be reached by the eddy current probe 118.

When the flexible part 114 has been shaped, the eddy current probe 118 then simply has to be applied against the surface of the measurement area. In the case of FIG. 3, the flexible part 114 is shaped for the measurement areas B1 and B4.

Depending on the measurement areas, it is possible to move the eddy current probe 118 from one area to another by rotating the straight part 112 through 180° about its longitudinal axis.

The shaping of the flexible part 114 provides easy access to all the parts of the structure 103 to be tested. In particular, in the case of the thrust reverser 100, there is no need to remove the protective casings.

The flexible part 114 is sufficiently flexible to be easily shaped by a technician by pressing against the template 302, 402, and is sufficiently rigid to retain its shape after shaping, without any intervention by the technician. The flexible part 114 is, for example, of the flexible cable type, composed of articulated parts.

Figure 5:
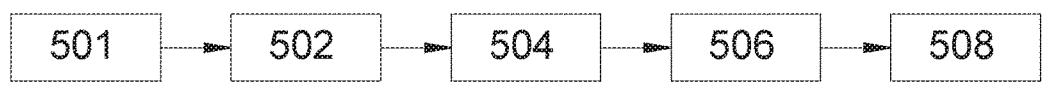
FIG. 5 is a flow diagram of the test method as claimed in the invention.

FIG. 5 shows an algorithm of a method 500 for testing the integrity of a component (in this case the frame 102d) in a measurement area of the component, the method comprising:

a selection step 502 in which a technician selects a template 302, 402 corresponding to the measurement area, a shaping step 504 in which the technician shapes the flexible part 114 against the template 302, 402 thus selected, a positioning step 506, in which the technician positions the instrument 110 thus shaped so that the eddy current probe 118 is placed in the measurement area, and a measurement step 508, in which the technician makes a measurement by means of the eddy current probe 118 which has been thus positioned.

In a particular embodiment, the test method 500 comprises, before the selection step 502, a production step 501 in which the template 302, 402 corresponding to the measurement area A1-2, B1-4, C1-4, D1-2 is fabricated on the basis of the geometry of the measurement area A1-2, B1-4, C1-4, D1-2 to be reached.

The measurement step 508 is performed using an appropriate measuring apparatus. For this purpose, electrical conductors run along the instrument 110 from the eddy current probe 118 to the measuring apparatus.

The set of templates 302, 402 and the instrument 110 including the eddy current probe 118 form a toolkit.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for testing the integrity of a component using an instrument having a straight part, a flexible part, and a rigid end part following the flexible part, the rigid end part carrying an eddy current probe, said component comprising a plurality of measurement areas each configured to be contacted by the eddy current probe in order to test the integrity of the component, the method comprising the steps:

selecting a first template from a plurality of templates, each template from the plurality of templates corresponding to at least one measurement area, the first template from the plurality of templates corresponding to at least two measurement areas of said component, the at least two measurement areas being separated, shaping the flexible part against the first template so as to provide the eddy current probe with an orientation relative to the at least two measurements areas, positioning the instrument so that the eddy current probe is placed in a first measurement area of the at least two measurements areas while retaining a shape of the flexible part, provided from the first template and retaining the orientation of the eddy current probe, measuring an eddy current of the first measurement area via the eddy current probe; and rotating the straight part of the instrument about a longitudinal axis so as to move the eddy current probe from the first measurement area to a second measurement area from the at least two measurement areas while retaining the shape of the flexible part; and, measuring an eddy current of the second measurement area via the eddy current probe.

2. The test method as claimed in claim 1, further comprising, before the selecting step, a step of fabricating the first template corresponding to the first measurement area.

3. The test method as claimed in claim 1, wherein the straight part of rotated 180° about the longitudinal axis.

4. The method of claim 1, wherein each template from the plurality of templates corresponds to two measurement areas of said component.

5. A toolkit comprising:

an instrument having a straight part, a flexible part, and a rigid end part following the flexible part, the rigid end part carrying an eddy current probe, and a plurality of templates configured to shape the flexible part, each template from the plurality of templates configured to provide the eddy current probe with an orientation corresponding to at least one measurement area of a component comprising a plurality of measurement areas, wherein at least a first template is configured to provide a first orientation that corresponds to at least two measurement areas, and wherein the flexible part is sufficiently rigid to maintain a shape of the flexible part relative to the orientation of the eddy probe after the flexible part has been shaped, and, the at least two measurement areas separated so that upon a rotation of the straight part, the eddy current probe moves from a first measurement area of the at least two measurement areas to a second measurement area of the at least two measurement areas while the orientation of the eddy probe is retained and the shape of the flexible part is retained.

6. The toolkit of claim 5, wherein each template from the plurality of templates corresponds to two measurement areas of said component.

7. A method for testing the integrity of a component using an instrument having a straight part, a flexible part, and a rigid end part following the flexible part, the rigid end part carrying an eddy current probe, said component comprising a plurality of measurement areas each configured to be contacted by the eddy current probe in order to test the integrity of the component, the method comprising the steps:

selecting a first template corresponding to a first measurement area of the component, shaping the flexible part against the first template to provide the flexible part with a first shape relative to the eddy current probe and to provide the eddy current probe with an orientation relative to at least two measurement areas, positioning the instrument so that the eddy current probe is placed in a first measurement area of the at least two measurement areas while retaining of the first shape of the flexible part and the orientation of the eddy current probe, measuring an eddy current of the first measurement area of said component, rotating the straight part about a longitudinal axis to move the eddy current probe from the first measurement area to a second measurement area of the at least two measurement areas while the orientation of the eddy current probe is retained, and measuring an eddy current of the second measurement area of said component.

8. The method of claim 7 further comprising:

selecting a second template corresponding to at least a third measurement area of said component, shaping the flexible part against the second template to provide the flexible part with a second shape relative to the eddy current probe and to provide the eddy current probe with a second orientation relative to the third measurement area, positioning the instrument so that the eddy current probe is placed in the third measurement area of said component while retaining of the second shape of the flexible part and the second orientation of the eddy current probe, and measuring an eddy current of the third measurement area of said component via the eddy current probe.

9. The method of claim 8 further comprising: after measuring the eddy current of the third measurement area of said component, rotating the straight part of the instrument so as to position the eddy current probe in a fourth measurement area of said component while retaining of the second shape of the flexible part and the second orientation of the eddy current probe, and measuring an eddy current of the fourth measurement area of said component via the eddy current probe.

* * * * *